United States Patent
Raghuveer et al.

(10) Patent No.: US 12,343,194 B2
(45) Date of Patent: Jul. 1, 2025

(54) SYSTEM AND METHOD OF MONITORING ULTRASOUND TESTS

(71) Applicant: Neurasignal, Inc., Los Angeles, CA (US)

(72) Inventors: Madala Naveen Raghuveer, Vinukonda (IN); Sivasankaran Krishnan, Bengaluru (IN); Rahul Radhakrishnan, Alappuzha (IN); Nithya Lakshmi Santhosh Kumar, Bengaluru (IN)

(73) Assignee: Neurasignal, Inc., Los Angeles, CA (US)

( * ) Notice: Subject to any disclaimer, the term of this patent is extended or adjusted under 35 U.S.C. 154(b) by 600 days.

(21) Appl. No.: 17/712,019

(22) Filed: Apr. 1, 2022

(65) Prior Publication Data

US 2023/0225697 A1 Jul. 20, 2023

(51) Int. Cl.
*A61B 8/06* (2006.01)
*A61B 8/00* (2006.01)
*G16H 40/67* (2018.01)
*G16H 50/30* (2018.01)

(52) U.S. Cl.
CPC ............ *A61B 8/06* (2013.01); *A61B 8/488* (2013.01); *A61B 8/5223* (2013.01); *G16H 40/67* (2018.01); *G16H 50/30* (2018.01)

(58) Field of Classification Search
CPC ......... A61B 8/06; A61B 8/455; A61B 8/5223; G16H 40/67; G16H 50/30
See application file for complete search history.

(56) References Cited

U.S. PATENT DOCUMENTS

| | | | |
|---|---|---|---|
| 7,604,599 B2 * | 10/2009 | Mozayeni | A61B 5/02007 600/457 |
| 2004/0002654 A1 * | 1/2004 | Davidson | A61B 5/7264 977/905 |
| 2004/0267127 A1 * | 12/2004 | Abend | G01S 15/8993 600/450 |
| 2010/0152563 A1 * | 6/2010 | Turner | A61B 5/14535 600/364 |
| 2019/0209141 A1 * | 7/2019 | O'Brien | A61B 8/5223 |
| 2019/0216433 A1 * | 7/2019 | Hamilton | A61B 8/488 |
| 2019/0254584 A1 * | 8/2019 | Atlas | A61B 8/5223 |

FOREIGN PATENT DOCUMENTS

WO WO-2008060328 A2 * 5/2008 ......... G06F 19/3418

* cited by examiner

*Primary Examiner* — Boniface N Nganga
(74) *Attorney, Agent, or Firm* — Polygon IP, LLP

(57) ABSTRACT

A method and system for monitoring ultrasound tests and notifying users about test results, are described. The method includes receiving ultrasound test data representing blood flow in a blood vessel, and receiving a notification condition having a flow parameter threshold for the blood flow. The method includes determining whether the ultrasound test data meets the notification condition, and transmitting, in response to the ultrasound test data meeting the notification condition, a notification. The notification is sent in real-time, concurrently with the ultrasound test, and includes a selectable reference to cause the display of the test results on a user device. Other embodiments are also described and claimed.

20 Claims, 10 Drawing Sheets

SYSTEM AND METHOD OF MONITORING ULTRASOUND TESTS

CROSS-REFERENCE TO RELATED APPLICATIONS

The present application claims priority to and the benefit of Indian Patent Application No. 202221002400, filed on Jan. 14, 2022, the disclosure of which is hereby incorporated by reference in its entirety.

BACKGROUND

Field

The present disclosure relates to systems and methods for monitoring ultrasound tests and, more specifically, systems and methods for monitoring transcranial Doppler ultrasound tests.

Background Information

Ultrasound imaging is used in medicine to non-invasively examine the health and function of the human body. For example, transcranial Doppler (TCD) can be used to measure the velocity of blood flow in a neurovasculature of a patient. Currently, TCD ultrasound examinations are typically performed by a sonographer using a transducer of a TCD ultrasound machine to identify and insonate a region of vasculature. Echoes of ultrasound waves insonating the region of vasculature are received and analyzed by the TCD ultrasound machine, and the test results are displayed on the TCD ultrasound machine for observation by the sonographer (or stored for later review by a medical practitioner). The medical practitioner may use the displayed test results to diagnose aneurysms, vasospasms, and other health problems.

SUMMARY

Existing transcranial Doppler (TCD) ultrasound machines can be used by medical practitioners to view ultrasound test results in real-time, concurrently with the TCD ultrasound examination. The medical practitioner must be present at the examination, however, and are not notified when test results meet certain conditions, e.g., when emboli counts exceed a predetermined threshold level for a predetermined threshold time. In other words, existing systems do not monitor ultrasound test results to provide real-time, condition-based notifications to remote users when their attention and input may be needed. Accordingly, there is a need for an ultrasound test monitoring system that monitors, e.g., continuously and in real-time, ultrasound test data, and notifies users based on thresholds or conditions that are preset by the users.

A method of monitoring ultrasound test results is provided herein. In an embodiment, the method includes receiving ultrasound test data representing blood flow in a blood vessel. The ultrasound test data can be generated, for example, by a TCD ultrasound machine. Notification conditions can also be received. For example, a user can input the notification condition through a front-end user interface of an ultrasound test monitoring system. The notification conditions can have a flow parameter threshold including a threshold level for a blood flow parameter of the blood flow. For example, the blood flow parameter can be a mean velocity, a pulsatility index, or an emboli count of the blood flow, and the threshold level can be an upper threshold or a lower threshold of the blood flow parameter. The method includes determining whether the ultrasound test data meets the notification condition. In an embodiment, the ultrasound test data meets the notification condition when the ultrasound test data meets the flow parameter threshold. In response to determining that the notification condition is met, the method includes transmitting a notification. The notification can indicate that the notification condition is met, and can include a selectable reference that links to the ultrasound test data. For example, the selectable reference can be selected by the user to cause display of a test data page. The user can then review the test data that triggered the notification.

The flow parameter threshold can include, in addition to the blood flow parameter, criteria such as a location of the blood vessel, or a flow parameter threshold indicating whether the threshold level is an upper threshold or a lower threshold. The notification condition can also include a time threshold over which the flow parameter threshold must be met to trigger the notification. Accordingly, the notification can be sent based on several conditions and/or thresholds that reduce a likelihood of false positive/negative notifications.

In an embodiment, the method is performed in real-time, concurrently with the ultrasound examination. For example, the notification can be transmitted within 250 milliseconds of receiving the ultrasound test data. The method can be executed by the ultrasound test monitoring system having a distributed cloud architecture that allows for such real-time monitoring. Accordingly, the method and system allows remotely located medical teams to provide timely care to patients.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

DETAILED DESCRIPTION

Embodiments describe a system and method of monitoring ultrasound tests and notifying users about test results. The system and method can be used to provide real-time threshold or condition-based notifications to users that are not present at a transcranial Doppler (TCD) ultrasound test, for example, concurrently with the transcranial Doppler TCD ultrasound test. However, the system and method may also be used to monitor other ultrasound or medical imaging tests. Thus, reference to the system as being used for monitoring any particular medical test is not limiting.

In an aspect, a system and method of providing real-time monitoring of an ultrasound test, is provided. The system and method can generate threshold- or condition-based notifications that can be sent to a user concurrently with the ultrasound test. For example, the notification can be triggered by a blood flow parameter meeting a predetermined criteria for a predetermined period of time. The notification can reach the user, remotely, within several seconds of the criteria being met, and thus, the user can provide timely review and input to promote patient care. More particularly, the real-time notifications allow for telemedicine care teams and doctors monitoring patients remotely, outside of the examination room, to be alerted of any change in a patient's condition. Examples of such changes include a number of emboli or a flow velocity of brain blood flow being above or below a medically safe threshold.

Figure 1:
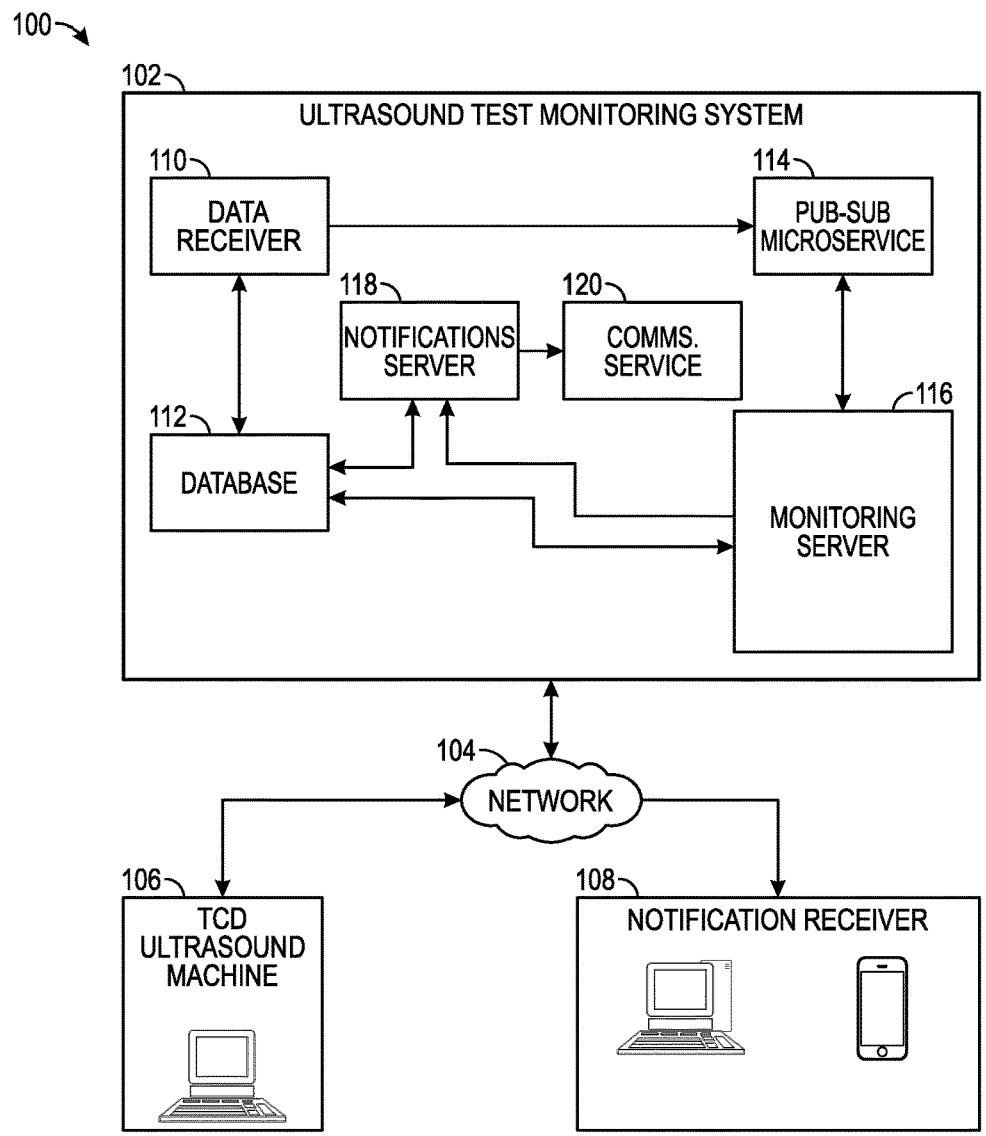
FIG. 1 is a block diagram of an example environment for monitoring ultrasound tests, in accordance with an embodiment.

Referring to FIG. 1, a block diagram of an example environment for monitoring ultrasound tests is shown in accordance with an embodiment. As shown, the environment 100 includes an ultrasound test monitoring system 102 that is interconnected with one or more user devices via a communications network 104. The communications network 104 may be the internet, a wide area network (WAN), intranet, or other suitable network. The ultrasound test monitoring system 102 may be hosted on one or more local servers, may be a cloud based system, or may be a hybrid system with local servers and in the cloud. The ultrasound test monitoring system 102 is maintained by engineers which develop features and tools, such as a front-end user interface having account views to set up notification criteria and test data views to display ultrasound test data.

In an embodiment, the environment 100 is a distributed system in which the ultrasound test monitoring system 102 is connected to a TCD ultrasound machine 106 and a notification receiver 108. The TCD ultrasound machine 106 is used to conduct a TCD ultrasound examination of a patient. The TCD ultrasound machine 106 can transmit live data of the examination to the ultrasound test monitoring system 102 via a computer communications protocol. It will be appreciated that the TCD ultrasound machine 106 is a non-limiting example of medical devices that can interact with the test monitoring system and that other medical devices, such as electrocardiogram (EKG) machines, can also be used. The ultrasound test monitoring system 102 can determine, based on the live data, whether a notification is triggered for a user, and responsively send the notification to the notification receiver. The notification receiver 108 can include any of various client devices, such as desktop devices, mobile devices, or any other devices that can receive the notification that is triggered by the live test data. The client devices can include web applications, email applications, mobile applications, text messaging applications, or other applications to receive and display the notifications to a user, such as a physician of the patient being examined by the TCD ultrasound machine 106.

Although FIG. 1 shows only a select number of computing devices and/or systems (e.g., one ultrasound test monitoring system 102, one TCD ultrasound machine 106, and two notification receiver devices 108), the environment 100 may include any number of computing devices and/or systems that are interconnected in any arrangement to facilitate the exchange of data between the computing devices and/or systems.

Figure 2:
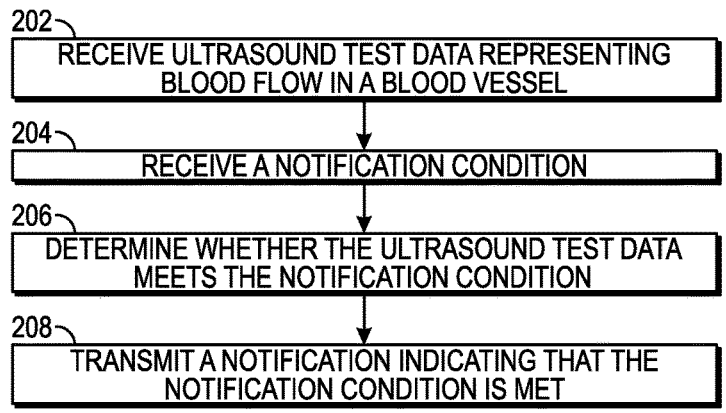
FIG. 2 is a flowchart of a method of monitoring an ultrasound test, in accordance with an embodiment.

The ultrasound test monitoring system 102 integrates several components that allow for the receipt of notification criteria and the generation of condition-based notifications based on ultrasound test data relative to the notification criteria. More particularly, the ultrasound test monitoring system 102 includes components that are configured to perform the method illustrated in FIG. 2. Furthermore, operations of the method of monitoring an ultrasound test shown in FIG. 2 are illustrated in FIGS. 3-12. Accordingly, the components of the ultrasound test monitoring system 102 shown in FIG. 1 and the operations of FIG. 2 shall be referred to and described in more detail within the description of the figures that follows.

Figure 3:
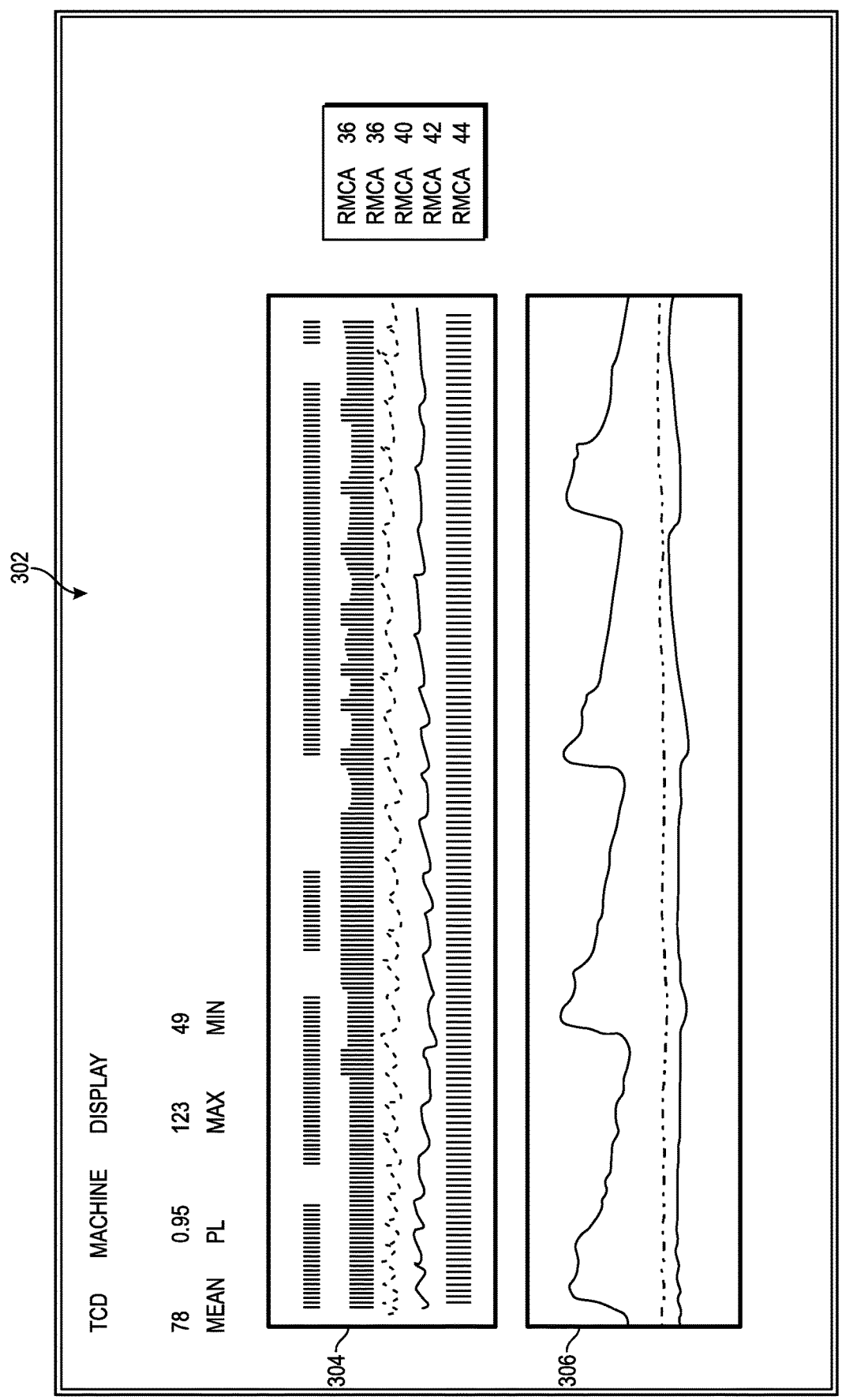
FIG. 3 is a pictorial view of ultrasound test data displayed on a user interface of a TCD ultrasound machine, in accordance with an embodiment.

Referring to FIG. 3, a pictorial view of ultrasound test data displayed on a user interface of a TCD ultrasound machine is shown in accordance with an embodiment. Ultrasound test data 302 can be generated by the TCD ultrasound machine 106. The ultrasound test data 302 can include one or more data sets representing blood flow in a blood vessel. For example, the illustrated test data can include measurements of blood flow in a left middle cerebral artery (MCA). It will be appreciated that the data can be measured at several locations within the head, on the left side and/or the right side of the head.

A first data set 304 can include M-mode data. The M-mode data can include time motion display of the ultrasound wave as it propagates through the neurovasculature. A second data set 306 can represent blood flow velocity at a selected depth relative to the first data set 304. More particularly, the waveform of the second data set 306 can show cerebral blood flow velocity (CBFV), which increases and decreases as the blood pressure within the neurovasculature oscillates. Accordingly, the first data set 304 can show Doppler over time, and the second data set 306 can include calculations of cerebral blood flow velocity.

In addition to the raw and calculated data shown in the first data set 304 and the second data set 306, derived data can be calculated to represent characteristics of the blood flow. For example, mean blood velocity, maximum blood velocity, minimum blood velocity, and pulsatility index can be calculated from the M-mode and CBFV data of the data sets. The data sets and the derived data can be based on data points collected at a predetermined interval, e.g., every 125 ms. Accordingly, at the predetermined interval the ultrasound test data 302, which can include the raw, calculated, and derived data, can be sent from the TCD ultrasound machine 106 to the ultrasound test monitoring system 102. Alternatively, the raw data can be sent at the predetermined interval, and the ultrasound test monitoring system 102 can calculate and derive additional data for use in monitoring, as described below.

At operation 202 (FIG. 2), the ultrasound test data 302 is received by the ultrasound test monitoring system 102. For example, the ultrasound test monitoring system 102 can include a data receiver 110 (FIG. 1) to receive the ultrasound test data 302. The TCD ultrasound machine 106 can send the ultrasound test data 302 in packets via WebSocket, e.g., 250 packets per second, which are received by the data receiver 110. The data receiver 110 component can be a streaming server, e.g., a streaming API, that continuously receives the ultrasound test data 302 from the TCD ultrasound machine 106 and directs the received data to one or more other components for use in the monitoring method. For example, the streaming server can receive the Doppler and/or CBFV data and direct the data to one or more microservices of the system to have the mean velocity, pulsatility index, or other flow data calculated.

Figure 4:
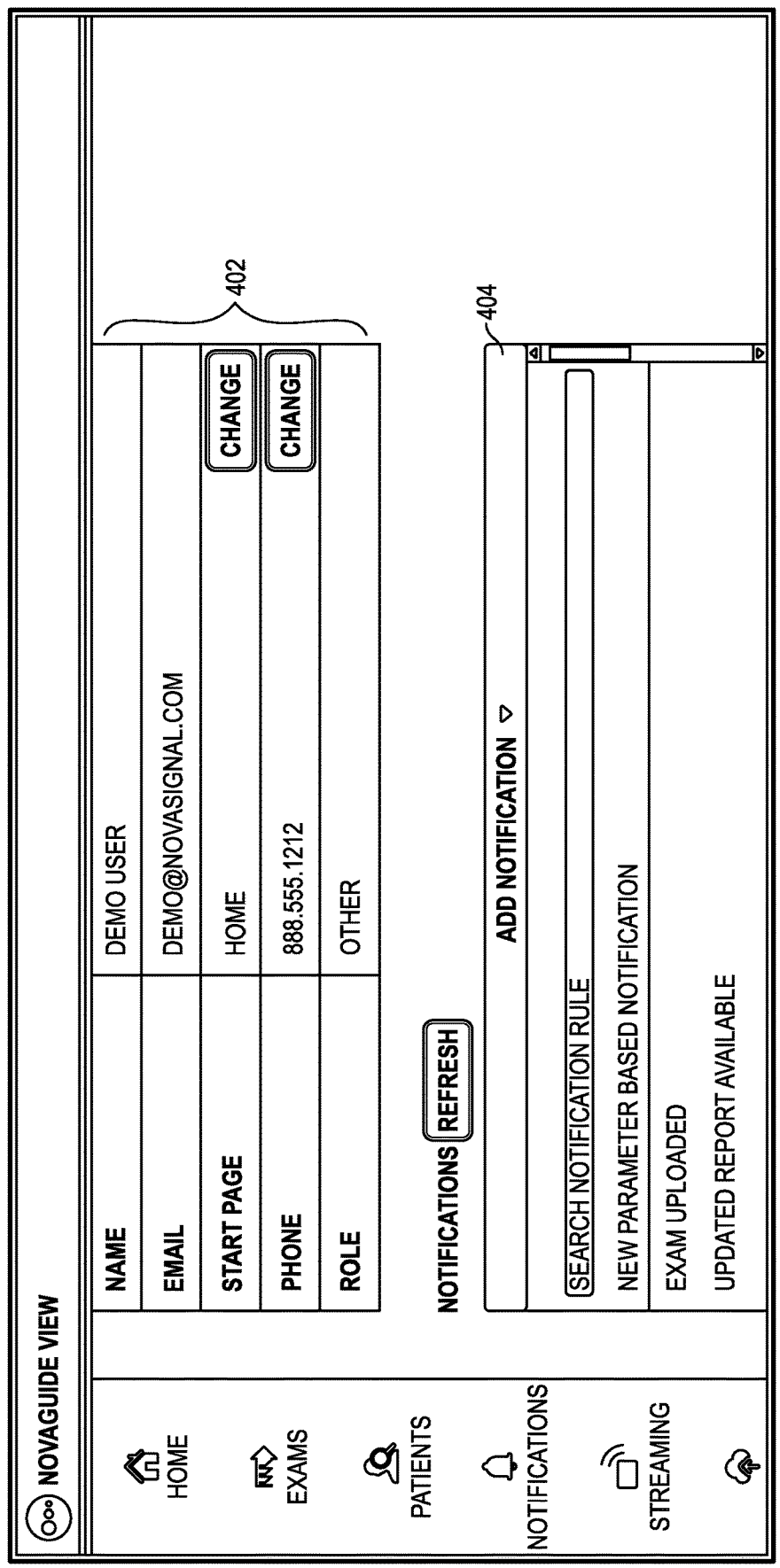
FIG. 4 is a pictorial view of an account view of a user interface, in accordance with an embodiment.

Referring to FIG. 4, a pictorial view of an account view of a user interface is shown in accordance with an embodiment. At operation 204 (FIG. 2), the ultrasound test monitoring system 102 receives a notification condition. The notification condition can be set through a front-end user interface. For example, the user interface can be implemented in a progressive web application, a native mobile applications, etc., which the user can access to set notification conditions. As shown, the account view can display user profile information 402, such as a name and email of the user. The user profile information 402 can also include a preferred start page, a phone number, and a role of the user within an organization. In an embodiment, the user can use the account view of the user interface to initiate the addition of a notification condition. More particularly, the user can select an add notification element 404 to cause the user interface to display a notification settings view through which notification conditions may be added.

Figure 5:
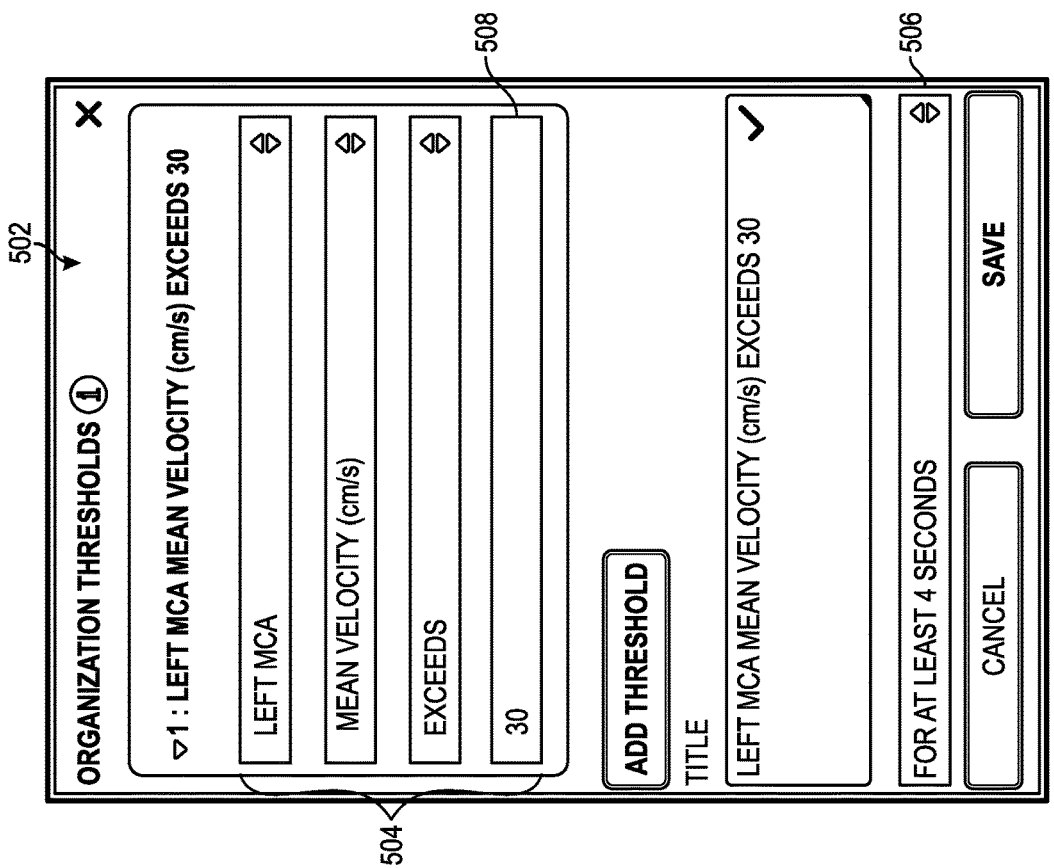
FIG. 5 is a pictorial view of a notification settings view of a user interface, in accordance with an embodiment.

Referring to FIG. 5, a pictorial view of a notification settings view of a user interface is shown in accordance with an embodiment. In response to a user selection of the add notification element 404, a notification condition interface can be displayed by the front-end application of the ultrasound test monitoring system 102. The notification condition interface can allow a notification condition 502 to be set. The notification condition 502 can include a flow parameter threshold 504 and/or a time threshold 506, which may be set by the user to trigger a notification based on the real-time data being continuously received from the TCD ultrasound machine 106. The flow parameter threshold 504 may include a threshold level 508 for the monitored blood flow parameter. For example, in the illustrated example, the notification condition 502 can trigger a notification when the mean velocity of blood flow (blood flow parameter) in a left MCA exceeds 30 cm/s (threshold level 508). The notification condition 502 may also include the time threshold 506 of at least 4 seconds, and thus, the notification may only be issued when the flow parameter threshold 504 meets the criteria for at least 4 seconds. Setting the time threshold 506 can avoid false positive/negative alerts by ensuring that notifications are generated in response to actual physical deviations, rather than merely transient data artifacts or examination errors. The selection of condition parameters can be made through drop down menus, as described below.

Figure 6:
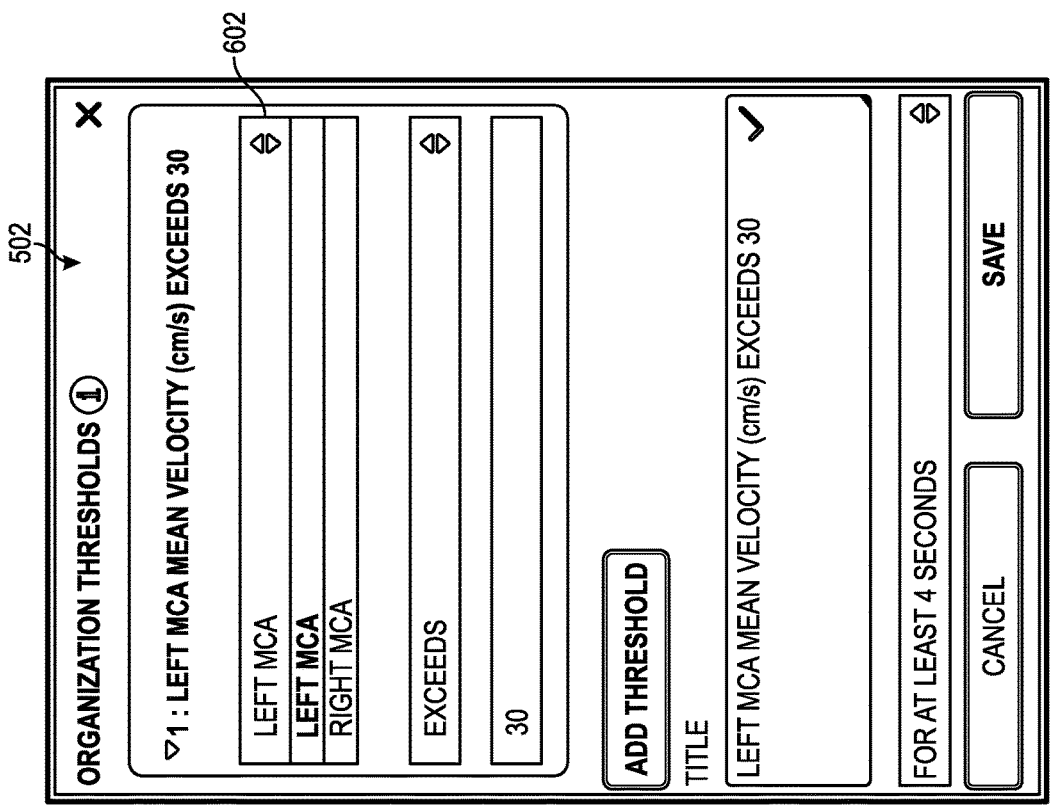
FIG. 6 is a pictorial view of a notification settings view having a location selector, in accordance with an embodiment.

Referring to FIG. 6, a pictorial view of a notification settings view having a location selector is shown in accordance with an embodiment. In an embodiment, the flow parameter threshold 504 includes a location 602 of a blood vessel. The user can interact with a drop down menu or otherwise select a predetermined location 602, such as a left MCA or right MCA of the neurovasculature. In an embodiment, the user may enter the location 602 through an alphanumeric input, rather than selecting predetermined locations 602.

Figure 7:
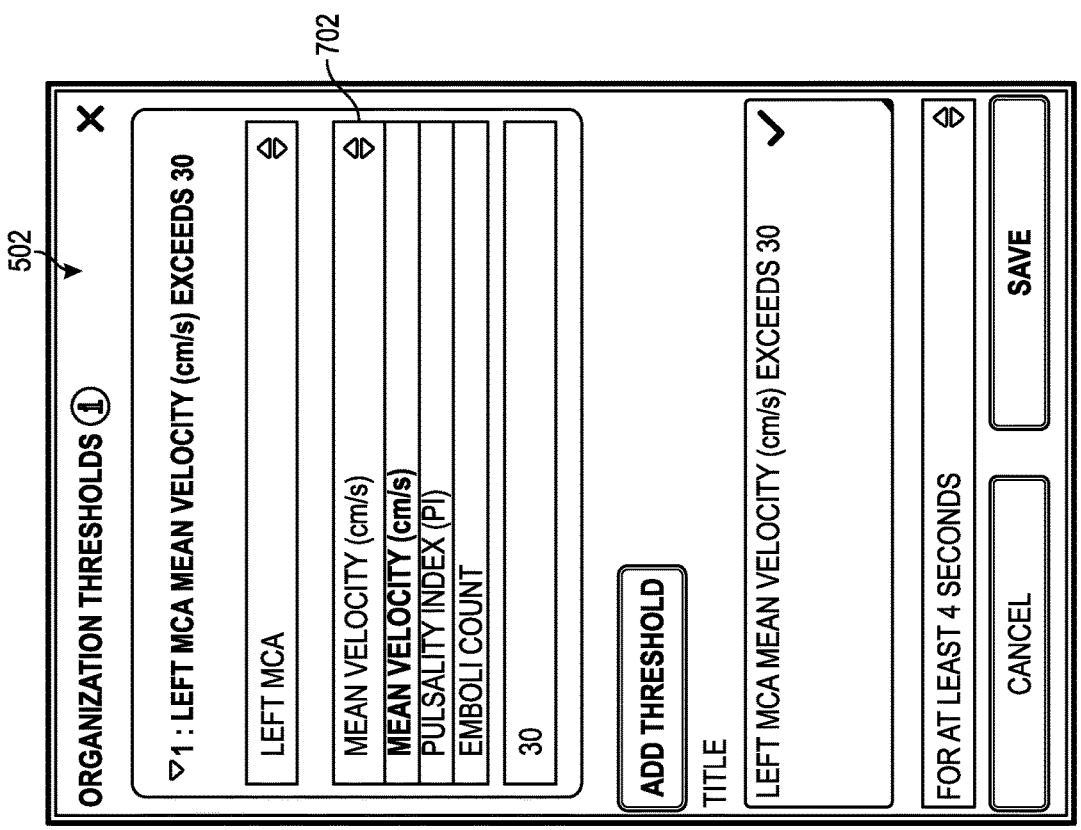
FIG. 7 is a pictorial view of a notification settings view having a blood flow parameter selector, in accordance with an embodiment.

Referring to FIG. 7, a pictorial view of a notification settings view having a blood flow parameter selector is shown in accordance with an embodiment. The flow parameter threshold 504 of the notification condition 502 can include a blood flow parameter 702 of the blood flow. The blood flow parameter 702 can include one or more of a mean velocity of the blood flow, a pulsatility index of the blood flow, or an emboli count of the blood flow. The mean velocity of the blood flow can be an average of the blood flow velocity over a predetermined period of time. The pulsatility index can be the difference between peak systolic flow and minimum diastolic flow over a predetermined period of time. The emboli count can be a number of emboli detected in the blood flow at the location of measurement over a predetermined period of time.

The blood flow parameters 702 can be useful in the detection of health problems. For example, the user may follow a medical protocol that assigns an increased risk of stroke to patients that present with 5 or more emboli per hour. Accordingly, the user may request notification whenever this blood flow parameter 702 is detected.

Figure 8:
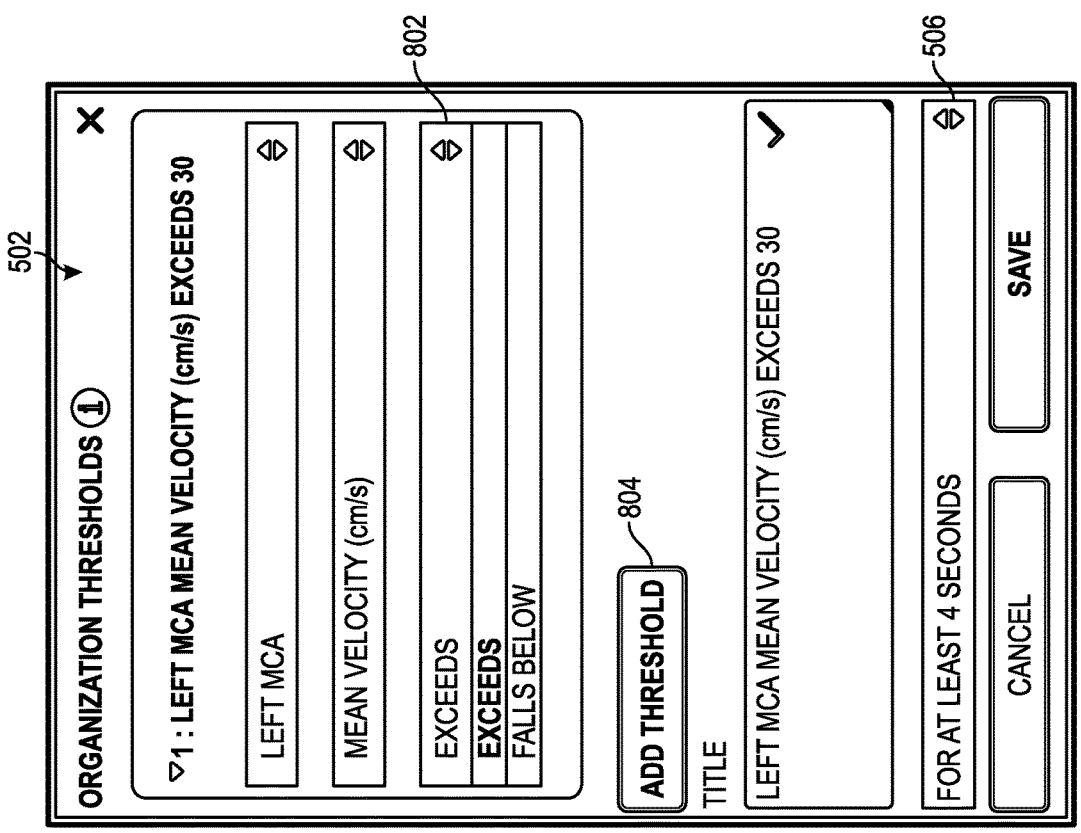
FIG. 8 is a pictorial view of a notification settings view having a threshold parameter selector, in accordance with an embodiment.

Referring to FIG. 8, a pictorial view of a notification settings view having a threshold parameter selector is shown in accordance with an embodiment. The flow parameter threshold 504 of the notification condition 502 can include a threshold parameter 802. The threshold parameter 802 can indicate whether the threshold level 508 is an upper threshold or a lower threshold for the blood flow parameter 702. For example, when the user selects "falls below," the threshold level 508 is an upper threshold that is met whenever the blood flow parameter value is less than the designated threshold level 508. By contrast, when the user selects "exceeds," the threshold level 508 is a lower threshold that is met whenever blood flow parameter value is above the designated threshold level 508. Accordingly, the threshold level 508 can be a high-end or a low-end of a range of triggering values.

As described above, the notification condition 502 may also allow for a selection of a time threshold 506. For example, the drop-down selector of the user interface may allow the user to select time thresholds of 4 to 12 seconds. The time threshold 506 can designate a predetermined period of time over which the flow parameter threshold 504 must be met in order to meet the notification condition 502 and trigger a notification to the user.

A notification condition 502 can include one or more flow parameter thresholds 504. For example, the user may select and add threshold element 804 in the user interface to cause a second grouping of flow parameter threshold 504 to display within the notification condition 502. The second flow parameter threshold 504 (not shown) can have similar settings to the first flow parameter threshold 504 shown in FIGS. 5-8. For example, the second flow parameter threshold 504 can have a second threshold level 508, e.g., 5, for a second blood flow parameter 702, e.g., emboli count. Accordingly, while the first flow parameter threshold 504 of the notification condition 502 can trigger a notification when the mean velocity of blood flow (blood flow parameter 702) exceeds 30 cm/s (threshold level 508) over the threshold time 506, the second flow parameter threshold 504 of the notification condition 502 can trigger a notification when the emboli count (blood flow parameter) exceeds 5 emboli (threshold level) over the threshold time 506.

The flow parameter thresholds 504 of the notification condition 502 may be logically combined to trigger the notification. For example, the user interface may allow for the first flow parameter threshold 504 and the second flow parameter threshold to be combined by an AND or an OR logical operator. More particularly, when combined by an AND logical operator, both the first flow parameter threshold and the second flow parameter threshold must be present over the time threshold 506 to meet the notification condition 502. Alternatively, when combined by an OR logical operator, only one of the first flow parameter threshold or the second flow parameter threshold may be present over the time threshold 506 to meet the notification condition 502. It will be appreciated that other logical combinations of the flow parameter thresholds 504 may be used.

In an embodiment, each of the flow parameter thresholds 504 may be associated with a respective time threshold 506. In the examples provided above, the first flow parameter threshold 504 may have a time threshold 506 of at least 4 seconds, and thus, the threshold may be met when the mean velocity value is within the designated range for 4 seconds or more. By contrast, the second flow parameter threshold may have a respective time threshold of at least 30 minutes, and thus, the threshold may be met when the emboli count is within the designated range for 30 minutes or more.

Figure 9:
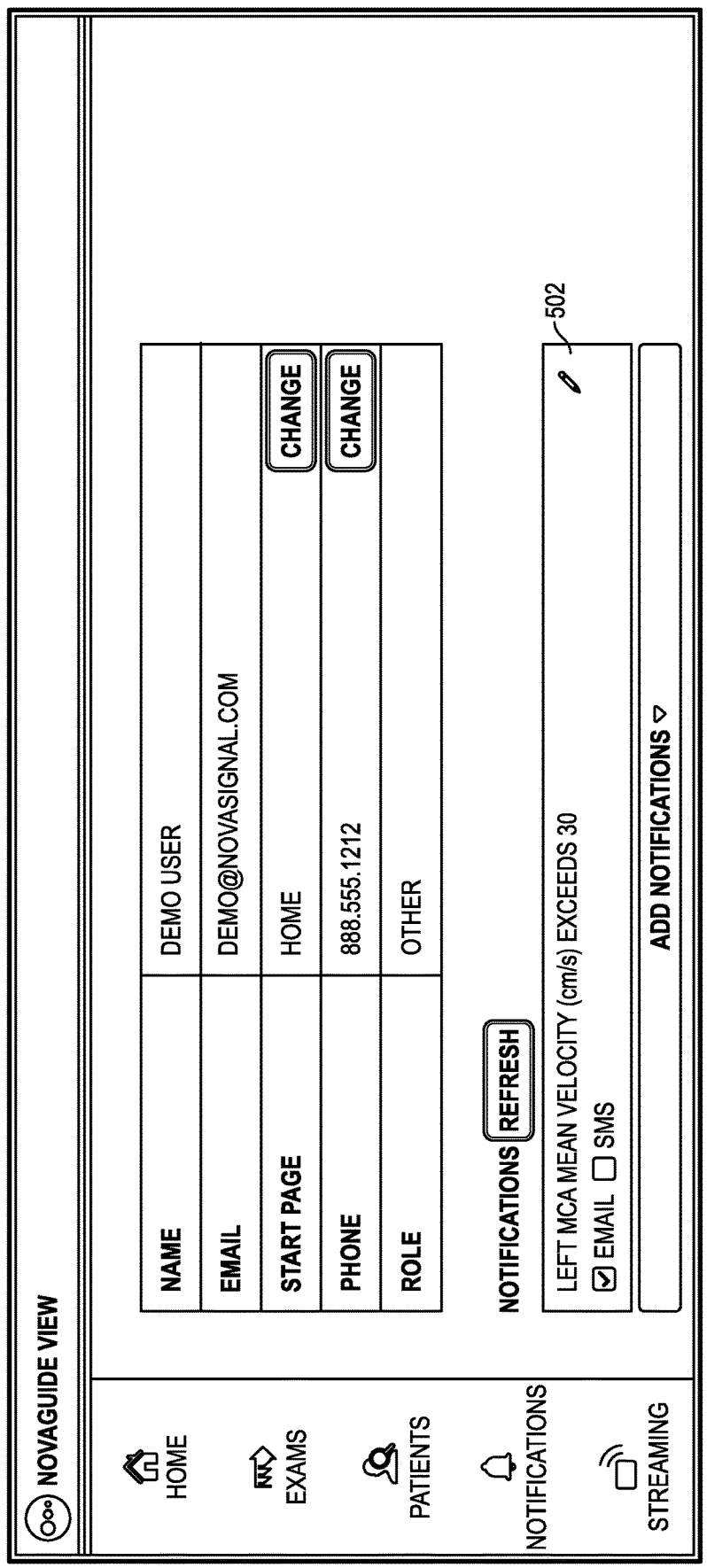
FIG. 9 is a pictorial view of an account view of a user interface, in accordance with an embodiment.

Referring to FIG. 9, a pictorial view of an account view of a user interface is shown in accordance with an embodiment. After entering the notification condition parameters, the user may save the notification condition 502. Saving the notification condition 502 can cause the notification settings view to close and the user interface can revert to the account view. As shown, the saved notification condition 502 can be displayed to the user in a notifications section of the account view. The user may subscribe to the notifications within the account view. For example, the notification condition 502 may be accompanied by checkboxes indicating a preference for an email notification or a text message notification. The user may check one or more of the boxes to subscribe to the notification condition 502. Accordingly, whenever a patient of the user presents with blood flow characteristics meeting the notification condition 502 during an ultrasound test, the user may be notified by email and/or text message. In an embodiment, the user interface can allow the user to select, on a patient-by-patient basis, which notification conditions 502 apply to which patients. Thus, the notification conditions 502 can be tailored by the user to apply to particular patient populations based on the user preference and medical practice or protocol.

The front-end application of the ultrasound test monitoring system 102 can allow users to set restrictions or filters on notification conditions 502. For example, a user may opt to receive notifications only during duty hours. More particularly, recipients of the notifications may be set by an administrator, and relevant members of the care team can be added or removed from the list of recipients based on time of day, calendared schedules, etc. Filters may also be set at multiple levels for one or more of the recipients. For example, the user or an administrator can set conditions using the front-end user interface to cause notification conditions 502 to include organization specific, TCD ultrasound machine specific, or patient specific criteria. For example, the administrator may set notification conditions 502, which when triggered, send notifications only to members of a particular care team. Likewise, the notifications may be filtered to be sent only to members of the care team that are associated with a particular machine or patient. For example, users may be automatically subscribed to events based on the patient returning to a hospital for an examination.

In an embodiment, restrictions or filters on notification conditions can be set through the account view of the user interface. The account page can include, for example, date selector elements, e.g., buttons, toggle elements, etc., that indicate days of the week. For example, the buttons can be associated with "weekdays," "weekends," or "Sunday, Monday, Tuesday, Wednesday, Thursday, Friday, and Saturday." Selection of the buttons can turn notifications on or off for the selected days or groups of days. The restriction/filter can also include a time window field to indicate, for each of the active days, the window of time during which notifications may be sent to the user. For example, the time window field can include a start time entry field and an end time entry field to designate the beginning and end of a notification time window. Accordingly, the user can enter or select a time for each day that will begin the notification time window, e.g., an on duty time, and a time for each day that will end the notification time window, e.g., an off duty time.

Referring again to FIG. 1, the ultrasound test monitoring system 102 can store the ultrasound test data 302 received by the data receiver 110, and the notification condition 502 received from the user through the front-end user interface in one or more databases 112. In an embodiment, the database(s) 112 stores details about the TCD ultrasound machine 106. The data receiver 110 microservice of the system can gather, e.g., fetch, the details from the database 112. For example, the data receiver 110 can request publish-subscribe topic names and subscription names for the TCD ultrasound machine 106 from the database 112. The database 112 can return the publish-subscribe topic and subscription names to the data receiver 110 for use in routing the incoming ultrasound test data 302 to a publish-subscribe microservice 114 of the ultrasound test monitoring system 102. Accordingly, as the data receiver 110 receives the ultrasound test data 302, the test data may be continuously relayed to the publish-subscribe microservice 114. More particularly, the ultrasound test data 302 may be published packet by packet (for example, at a rate of 250 packets per second) to the publish-subscribe topic.

The cloud-based distributed back-end of the ultrasound test monitoring system 102 can include other microservices to perform monitoring and notification functions. In an embodiment, the system includes a monitoring server 116. The monitoring server 116 can communicate with the publish-subscribe microservice 114 to continuously receive the published test data. For example, the monitoring server 116 can include a real-time monitoring API that concurrently receives data from the publish-subscribe microservice 114 and monitors that received data for triggering events.

To determine whether the triggering events occur, the monitoring server 116 can communicate with the database 112 to obtain notification conditions 502 from all users subscribed for the streaming session. The monitoring server 116 can request, e.g., fetch, the notification conditions 502 for the users that have subscribed to notifications for the patient prior to the ongoing ultrasound test. The database 112 can store the notification conditions 502 and subscription information received through the front-end user interface, and thus, the monitoring server 116 can receive the notification conditions 502, including the relevant flow parameter thresholds 504, for use in monitoring.

At operation 206 (FIG. 2), the ultrasound test monitoring system 102 can determine whether the ultrasound test data 302 meets the threshold(s) of the notification condition 502. The monitoring server 116 can observe the published test data at a predetermined rate, e.g., once per second, to determine whether the threshold(s) are met by the ultrasound test data 302. In an embodiment, determining whether the ultrasound test data 302 meets the threshold(s) includes determining whether the ultrasound test data 302 meets the flow parameter threshold 504 of the notification condition 502. For example, the monitoring server 116 can detect whether the first flow parameter threshold 504 (e.g., the mean velocity threshold) is within the threshold range defined by the notification condition 502. It will be appreciated that determining whether the ultrasound test data 302 meets each of the threshold(s) of the notification condition 502 can include determining whether several threshold(s) are met. For example, the monitoring server 116 can detect whether a second flow parameter threshold (e.g., the emboli count) is within the threshold range defined by the notification condition 502. As described above, determining whether the ultrasound test data 302 meets the threshold(s) can include determining whether the flow parameter threshold(s) are met for the time threshold 506.

In an embodiment, when the monitoring server 116 determines that the ultrasound test data 302 meets the threshold (s), the monitoring server 116 can communicate with a notification server 118 of the ultrasound test monitoring system 102. Monitoring server 116 may function to process each exam stream to check whether all threshold(s), with the logical operator between thresholds satisfy the notification condition 502. More particularly, the monitoring server 116 can determine whether the threshold(s) combine to meet a notification condition 502 necessitating the notification of users having the notification condition 502 set in their account preferences. Accordingly, the monitoring server 116 can communicate the triggered notification condition 502 to the notification server 118 to initiate a process through which the notification server 118 sends a notification to the users.

The notification server 118 can determine which users are subscribed to receive notifications for a triggered event. The notification server 118 can interact with the database 112 to obtain relevant information of all the users who registered for receiving notifications on such event. More particularly, the notification server 118 can communicate with the database 112 to obtain information about the users that should be notified of the notification condition 502 being met. The information can include the user email address or phone number, as entered in the account view of the user interface.

At operation 208 (FIG. 2), the notification server 118 can transmit, in response to determining that the ultrasound test data 302 meets the notification condition 502, a notification to all relevant users. The notification can indicate that the notification condition 502 is met. The architecture of the ultrasound test monitoring system 102 is such that the notification can be transmitted in real-time, concurrently with the ultrasound examination. Real-time may be considered to be a delay of less than one second between the occurrence of the event and the transmission of the notification. In an embodiment, the notification is transmitted within 250 ms of receiving the ultrasound test data 302. More particularly, no more than 250 ms elapses between operation 202 and operation 208. It has been shown that the ultrasound test monitoring system 102 can generate and transmit notifications within 50 ms of capturing the ultrasound test data 302, and thus, the ultrasound test monitoring system 102 qualifies as a real-time monitoring system.

In an embodiment, the notification server 118 can send the notification to all relevant users via an outbound communications service 120. The communications service 120 can connect with the notification receivers 108 over channels such as email, push notifications, text messaging (e.g., Short Messaging Service (SMS)), voice, or in-app messaging. The communication service can send the notification as a message that indicates to the receiving user that the notification condition 502 is met, and summarizes details of the triggering event.

Figure 10:
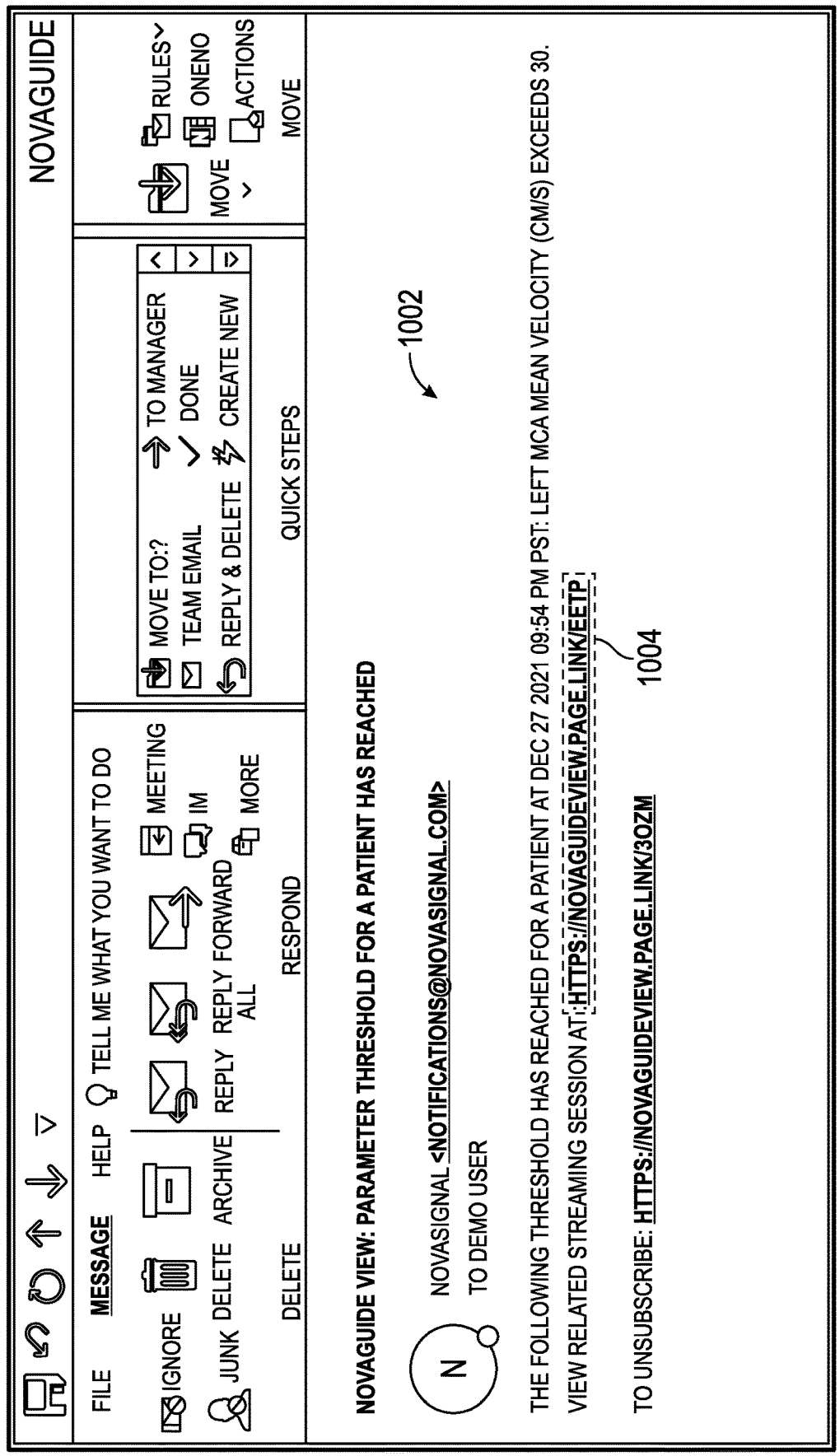
FIG. 10 is a pictorial view of an email notification, in accordance with an embodiment.

Referring to FIG. 10, a pictorial view of an email notification is shown in accordance with an embodiment. The user, e.g., the treating physician, can view a notification 1002 within an email application. The notification 1002 can include an email message having a subject line that summarizes the triggering event, e.g., "parameter threshold for a patient has reached." Furthermore, a body of the email message can contain details of the triggering event and/or notification condition 502, e.g., a time of the triggering event and/or "Left MCA Mean Velocity (cm/s) exceeds 50."

The notification 1002 may not include the ultrasound test data 302 on which the notification 1002 was triggered. In an embodiment, however, the notification 1002 includes a selectable reference 1004 to the ultrasound test data 302. The selectable reference 1004 may, for example, be a selectable hyperlink. The user may click or tap on the hyperlink to cause display of the ultrasound test data 302 within the email application or another application, such as the front-end user interface of the ultrasound test monitoring system 102. Accordingly, the notification 1002 can both notify the user of the triggering event and allow the user to quickly access the source data upon which the notification 1002 is based.

Figure 11:
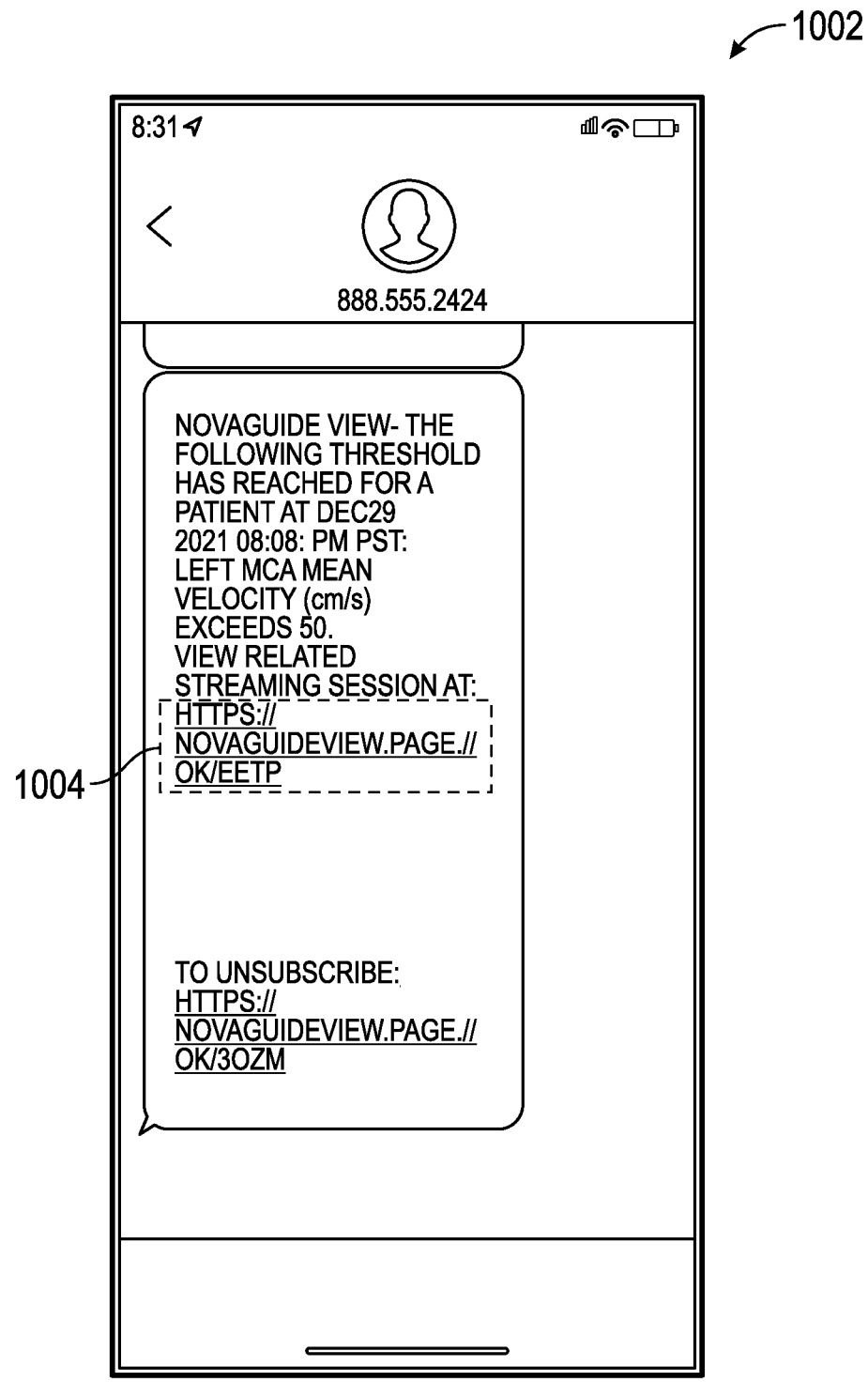
FIG. 11 is a pictorial view of a text message notification, in accordance with an embodiment.

Referring to FIG. 11, a pictorial view of a text message notification is shown in accordance with an embodiment. The notification 1002 may be sent as a text message, e.g., an SMS message. The text message can include the information described above with respect to the email message. More particularly, the text message can include a selectable reference 1004 to the ultrasound test data 302, and summarizing information about the triggering event. The user may also select a hyperlink within the text message to initiate a process unsubscribe from future notifications.

Figure 12:
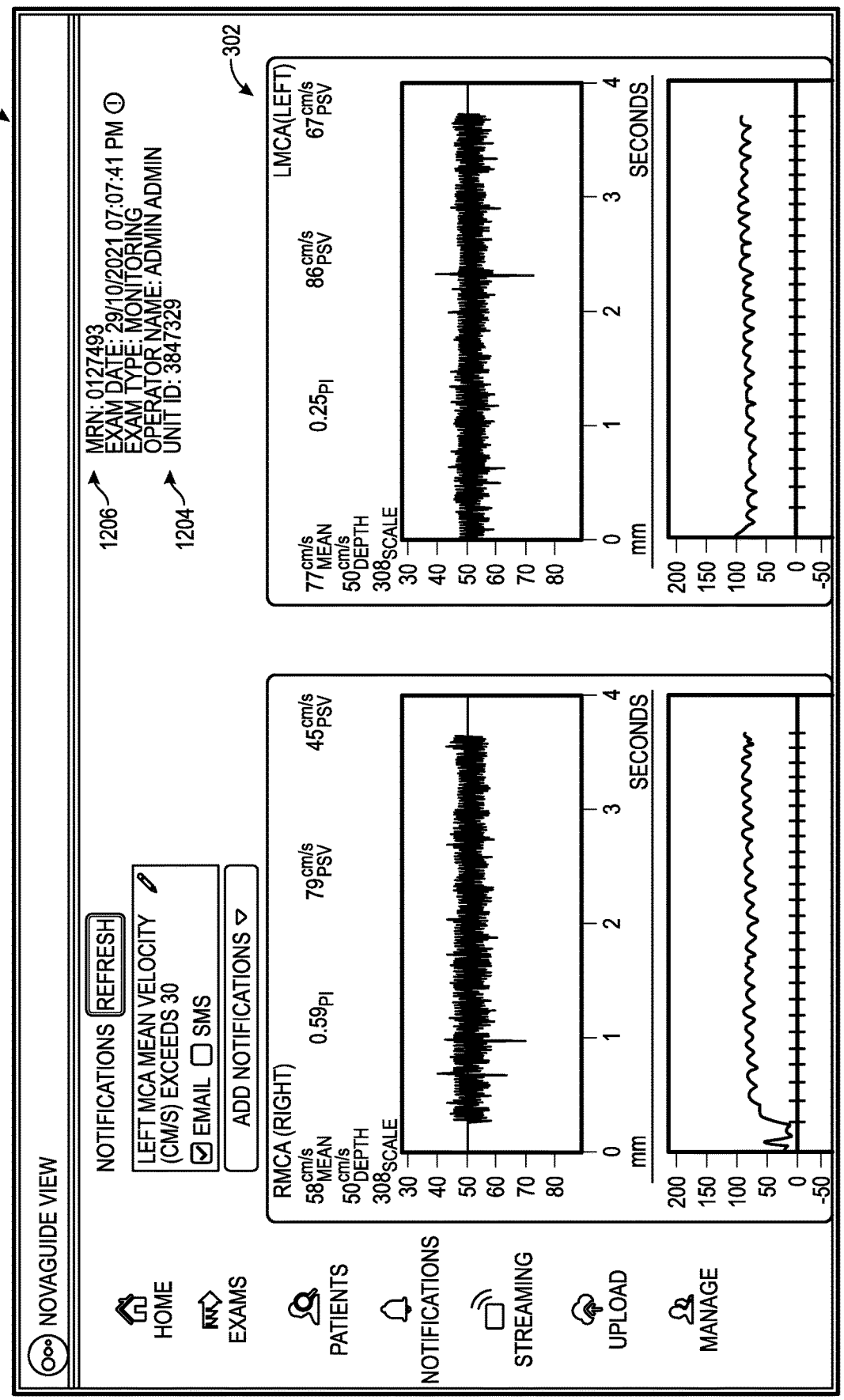
FIG. 12 is a pictorial view of a test data page of a user interface, in accordance with an embodiment.

Referring to FIG. 12, a pictorial view of a test data page of a user interface is shown in accordance with an embodiment. Selection of the selectable reference 1004 by the user can cause display of a test data page 1202. Accordingly, clicking on the hyperlink can open the test data page 1202 to allow the user to view the underlying ultrasound test data 302. More particularly, selecting the selectable hyperlink can initiate a process to launch an application, e.g., the front-end application of the ultrasound test monitoring system 102, to present relevant test information to the user. The process may require that the user log into the front-end application to authenticate the user and protect data privacy in the event that the notification 1002 was inadvertently sent to a wrong recipient.

The test data page 1202 may display the ultrasound test data 302 collected during the examination of the patient. For example, the test data page 1202 may display the first data set 304 and/or the second data set 306 generated by the TCD ultrasound machine 106. The test data page 1202 can include additional information that may be useful to the user. For example, the test data page 1202 may include a unit identifier 1204. The unit identifier 1204 can identify the TCD ultrasound machine 106 and ensure that any instructions from the physician (e.g., a request that blood thinners be delivered to a particular patient) are directed to the room having the correct TCD ultrasound machine 106. Similarly, the test page can include a medical record number 1206 of the patient being examined. Accordingly, the physician can obtain an instant report having the information needed to respond to the notification condition 502 to care for the patient.

As described above, the user or an administrator can set up a care team for each patient. Accordingly, the notification 1002 may be sent to several members of the care team, either simultaneously or consecutively. For example, the care team may have an escalation hierarchy including a primary recipient, e.g., a physician, and a secondary recipient, e.g., a physician assistant. In an instance in which the notification 1002 is sent to the physician and the physician does not respond to the notification 1002 within a predetermined period of time, the notification 1002 may then be sent to the physician assistant for attention. Accordingly, a fail-safe is provided to ensure that the notification 1002 is acknowledged by a member of the care team such that the patient is given appropriate attention.

In addition to storing the ultrasound test results for reference by the notification 1002 recipient, the ultrasound test monitoring system 102 may also store a log of the previously sent notifications 1002. The log may be stored, for example, in the database 112. The log can contain information about the sent notifications 1002, including contact information of the recipient, a time or date that the notification 1002 was sent, or information contained within the notification 1002 message. The log information may be maintained for later audits, e.g., by the organization performing the examinations.

Figure 13:
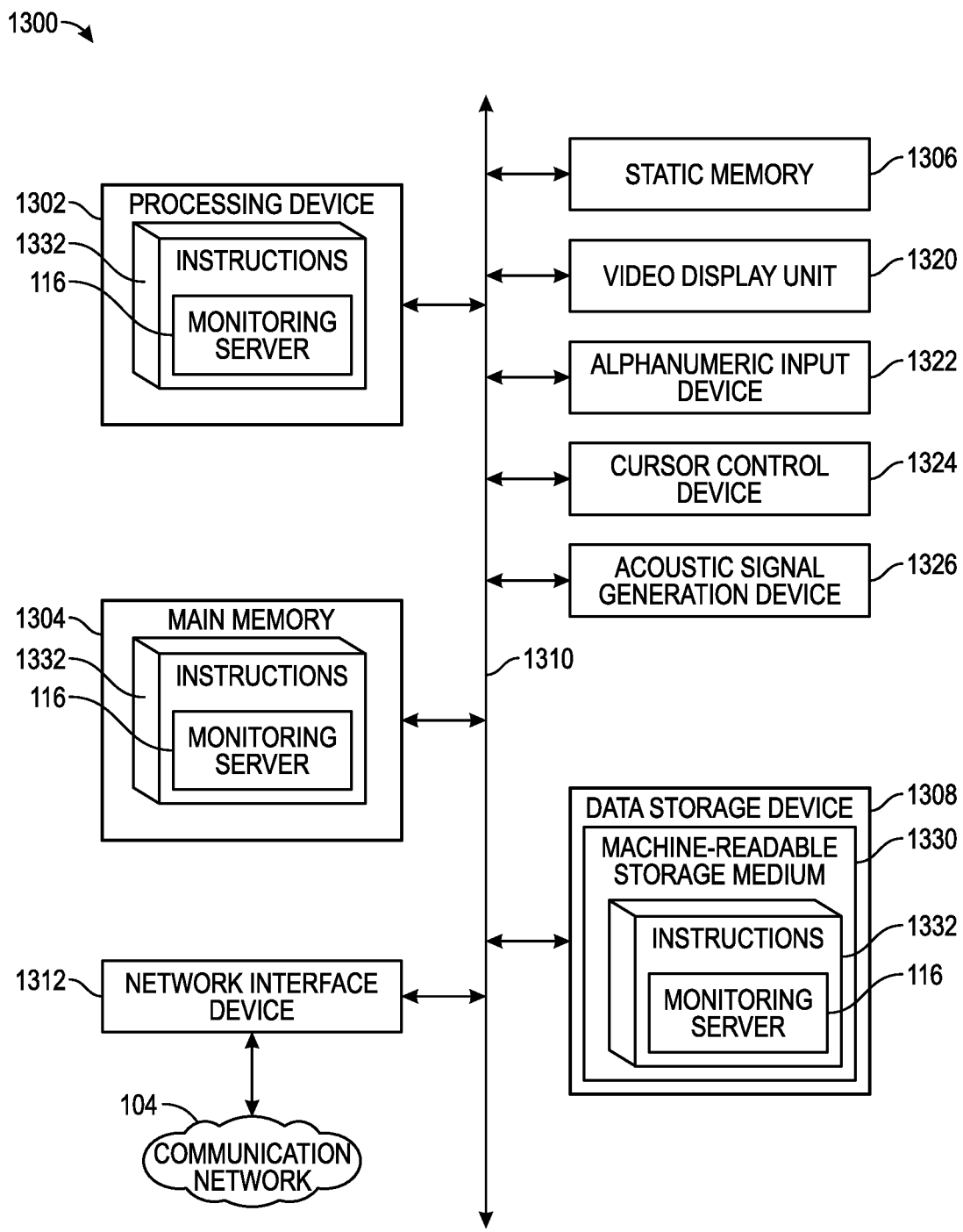
FIG. 13 is a block diagram of an example computing device that may perform one or more of the operations described herein, in accordance with an embodiment.

Referring to FIG. 13, a block diagram of an example computing device that may perform one or more of the operations described herein is shown in accordance with an embodiment. The ultrasound test monitoring system 102 (and/or TCD machine 106 or notification receiver 108) may include one or more computing devices 1300. Computing device 1300 may be connected to other computing devices in a LAN, an intranet, an extranet, and/or the Internet. The computing device may operate in the capacity of a server machine, e.g., computing system, or a client machine, e.g., remote client device, in a client-server network environment or in the capacity of a client in a peer-to-peer network environment. The computing device may be provided by a personal computer (PC), a set-top box (STB), a server, a network router, switch or bridge, or any machine capable of executing a set of instructions (sequential or otherwise) that specify actions to be taken by that machine. In some embodiments, while only a single computing device is illustrated, the term "computing device" may be taken to include any collection of computing devices that individually or jointly execute a set (or multiple sets) of instructions to perform the methods discussed herein.

The example computing device 1300 may include one or more processing devices (e.g., a general purpose processor, a PLD, etc.) 1302, a main memory 1304 (e.g., synchronous dynamic random access memory (DRAM), read-only memory (ROM)), a static memory 1306 (e.g., flash memory and a data storage device 1308), which may communicate with each other via a bus 1310.

Processing device 1302 may be provided by one or more general-purpose processing devices such as a microprocessor, central processing unit, or the like. In an illustrative example, processing device 1302 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 1302 may comprise one or more special-purpose processing devices such as an application specific integrated circuit (ASIC), a field programmable gate array (FPGA), a digital signal processor (DSP), network processor, or the like. The processing device(s) 1302 may be configured to execute the operations described herein, in accordance with one or more aspects of the present disclosure, for performing the operations and steps discussed herein.

Computing device 1300 may include a network interface device 1312 which may communicate with a communication network 104. The computing device 1300 may include a video display unit 1320 (e.g., a liquid crystal display (LCD) or a cathode ray tube (CRT)), an alphanumeric input device 1322 (e.g., a keyboard), a cursor control device 1324 (e.g., a mouse) and an acoustic signal generation device 1326 (e.g., a speaker). In one embodiment, video display unit 1320, alphanumeric input device 1322, and cursor control device 1324 may be combined into a single component or device (e.g., an LCD touch screen).

Data storage device 1308 may include a non-transitory computer-readable storage medium 1330 on which may be stored one or more sets of instructions 1332 that may include instructions for one or more components (e.g., one or more of the components or microservices of the ultrasound test monitoring system) for carrying out the operations described herein, in accordance with one or more aspects of the present disclosure. For example, instructions for the monitoring server 116 are illustrated by way of example, and not limitation. Instructions 1332 may reside, completely or at least partially, within main memory 1304 and/or within processing device 1302 during execution thereof by computing device 1300, main memory 1304 and processing device 1302 constituting computer-readable media. The instructions 1332 may be transmitted or received over the communication network 104 via network interface device 1312.

In an embodiment, the ultrasound test monitoring system 102 can suggest notification condition thresholds to a user based on past triggered notifications. For example, when the user selects the add notification element 404 of the account view (FIG. 4) and the front-end user interface transitions to the notifications setting view (FIG. 5) to allow the user to enter notification thresholds for a particular patient, the threshold fields may be prepopulated with threshold values that the user (or another user) previously set for patients having similar characteristics to the particular patient.

The method of suggesting notification thresholds can include determining prior patients that are similar to the particular patient. In an embodiment, examination data for the prior patients and the particular patient are stored in the database 112. The examination data can include medical parameters such as: demographic data of patients, e.g., age; raw data, e.g., blood flow curves; or derived data calculated based on the raw data, e.g., velocity curvature index. The ultrasound test monitoring system 102 can include an artificial intelligence (AI) and/or machine learning (ML) function that accesses the examination data and clusters patients based on the medical parameters. For example, the AI/ML function can determine a group of prior patients having demographic or derived medical parameters that are similar to the medical parameters collected for the particular patient during an examination. By way of example, the particular patient may have a given age and a diagnosis of stenosis, and so the AI/ML function may cluster prior patients within the same age group and diagnosis to derive suggested threshold values.

The method can include determining normal condition threshold values based on the similar prior patient notifications. The AI/ML function may further determine, for the clustered group, notification thresholds that are most commonly used for the group. For example, particular blood flow parameter threshold 504 values or time threshold 506 values may have been consistently used in notifications associated with the members of the clustered group. The AI/ML function can determine that the previously entered notification threshold values represent normal thresholds for similar patients, e.g., the particular patient.

The method can include suggesting the normal thresholds to a user during the setup of a new notification for the particular patient. For example, when the notification setting view (FIG. 5) is opened, the prepopulated fields of the notification condition 502 can include the blood flow parameter threshold 504 values and/or the time threshold 506 values determined to be normal from the prior patients. In the example illustrated in FIG. 5, the normal values can include the "left MCA mean velocity (cm/s) exceeds 30 for at least 4 seconds," as shown. It will be appreciated that, based on the suggestion, patients matched to a first group can cause a different set of threshold value suggestions to be generated as compared to patients matched to a second group. For example, the particular patient having the certain age and stenosis finding can cause suggested values to be displayed that differ from suggested values provided for a patient of a different age or lacking a stenosis.

The prepopulated fields may be suggestions, however, the fields may be changeable by the user. For example, the user may decide that a threshold level of 50 is preferred over 30 for a particular patient based on preferences or policies of the user or health organization. The user may adjust the suggested threshold value to a new value using the selection or entry mechanisms described above. The system may therefore recommend new threshold notifications to be set for a patient based on past triggered notifications for similar patients, which provides a fast and consistent process for establishing notifications.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method, comprising:
receiving a notification condition, the notification condition provided through an interface of a first user device and communicated by the first user device over a network, the notification condition provided through the interface via a first template by, at least in part, selecting one or more selectable conditions within the first template, the notification condition comprising a flow parameter threshold, the flow parameter threshold comprising a blood flow threshold level;
storing data associated with the notification condition within a database;
receiving, with a data receiver and from a first ultrasound machine separate from the first user device and for a first time period, ultrasound test data representing blood flow in a blood vessel, the ultrasound test data communicated by the ultrasound machine over the network to the data receiver;
analyzing the ultrasound test data to determine an identity of the first ultrasound machine;
determining, based on the identity of the ultrasound machine, that the notification condition is associated with the first ultrasound machine;
providing, based on the determining that the notification condition is associated with the first ultrasound machine, the notification condition to a monitoring server;
providing the ultrasound test data received over the first time period to the monitoring server at a predetermined rate;
determining, with the monitoring server, that the ultrasound test data meets the notification condition; and
transmitting, in response to determining that the ultrasound test data meets the notification condition, a notification indicating that the notification condition is met to a notification receiver device associated with and separate from the ultrasound machine, the notification transmitted over the network and provided according to a second template.

2. The method of claim 1, further comprising: receiving, with the data receiver and from the first ultrasound machine, the ultrasound test data; and relaying the ultrasound test data from the data receiver to a publish-subscribe microservice, wherein the providing the ultrasound test data comprises providing the ultrasound test data by the publish-subscribe microservice to the monitoring server.

3. The method of claim 2, wherein the data receiver relays the ultrasound test data to the publish-subscribe microservice on a packet by packet basis.

4. The method of claim 1, wherein the determining that the ultrasound test data meets the notification condition comprises determining that the ultrasound test data meets the flow parameter threshold.

5. The method of claim 4, wherein the notification condition further comprises a second flow parameter threshold having a second threshold level for a second flow parameter of the blood flow, and wherein determining that the ultrasound test data meets the notification condition further comprises determining that the ultrasound test data meets the flow parameter threshold and the second flow parameter threshold.

6. The method of claim 1, wherein the flow parameter threshold is associated with a location within the blood vessel.

7. The method of claim 1, wherein the flow parameter includes one or more of a mean velocity, a pulsatility index, or an emboli count of the blood flow.

8. The method of claim 1, wherein the flow parameter threshold includes a threshold parameter indicating whether the threshold level is an upper threshold or a lower threshold for the flow parameter.

9. The method of claim 1, wherein the notification condition comprises a time threshold, and wherein determining whether the ultrasound test data meets the notification condition includes determining whether the flow parameter threshold is met for the time threshold.

10. The method of claim 1, wherein the second template comprises a selectable reference to the ultrasound test data.

11. A non-transitory computer readable medium containing instructions, which when executed by one or more processors of an ultrasound test monitoring system, cause the ultrasound test monitoring system to perform a method, comprising:

receiving a notification condition, the notification condition provided through an interface of a first user device and communicated by the first user device over a network, the notification condition provided through the interface via a first template by, at least in part, selecting one or more selectable conditions within the first template, the notification condition comprising a flow parameter threshold, the flow parameter threshold comprising a blood flow threshold level;

storing data associated with the notification condition within a database;

receiving, with a data receiver and from a first ultrasound machine separate from the first user device and for a first time period, ultrasound test data representing blood flow in a blood vessel, the ultrasound test data communicated by the ultrasound machine over the network to the data receiver;

analyzing the ultrasound test data to determine an identity of the first ultrasound machine;

determining, based on the identity of the ultrasound machine, that the notification condition is associated with the first ultrasound machine;

providing, based on the determining that the notification condition is associated with the first ultrasound machine, the notification condition to a monitoring server;

providing the ultrasound test data received over the first time period to the monitoring server at a predetermined rate;

determining, with the monitoring server, that the ultrasound test data meets the notification condition; and transmitting, in response to determining that the ultrasound test data meets the notification condition, a notification indicating that the notification condition is met to a notification receiver device associated with and separate from the ultrasound machine, the notification transmitted over the network and provided according to a second template.

12. The non-transitory computer readable medium of claim 11, wherein the method further comprises: receiving, with the data receiver and from the first ultrasound machine, the ultrasound test data; and relaying the ultrasound test data from the data receiver to a publish-subscribe microservice, wherein the providing the ultrasound test data comprises providing the ultrasound test data by the publish-subscribe microservice to the monitoring server.

13. The non-transitory computer readable medium of claim 12, wherein the data receiver relays the ultrasound test data to the publish-subscribe microservice on a packet by packet basis.

14. The non-transitory computer readable medium of claim 11, wherein the determining that the ultrasound test data meets the notification condition comprises determining that the ultrasound test data meets the flow parameter threshold.

15. The non-transitory computer readable medium of claim 14, wherein the notification condition further comprises a second flow parameter threshold having a second threshold level for a second flow parameter of the blood flow, and wherein determining that the ultrasound test data meets the notification condition further comprises determining that the ultrasound test data meets the flow parameter threshold and the second flow parameter threshold.

16. The non-transitory computer readable medium of claim 11, wherein the flow parameter threshold is associated with a location within the blood vessel.

17. The non-transitory computer readable medium of claim 11, wherein the flow parameter includes one or more of a mean velocity, a pulsatility index, or an emboli count of the blood flow.

18. The non-transitory computer readable medium of claim 11, wherein the flow parameter threshold includes a threshold parameter indicating whether the threshold level is an upper threshold or a lower threshold for the flow parameter.

19. The non-transitory computer readable medium of claim 11, wherein the notification condition comprises a time threshold, and wherein determining whether the ultrasound test data meets the notification condition includes determining whether the flow parameter threshold is met for the time threshold.

20. The non-transitory computer readable medium of claim 11, wherein the second template comprises a selectable reference to the ultrasound test data.

* * * * *